United States Patent
Blick et al.

(10) Patent No.: US 9,488,600 B2
(45) Date of Patent: Nov. 8, 2016

(54) RADIO-FREQUENCY NANOPORE SENSOR

(71) Applicants: Wisconsin Alumni Research Foundation, Madison, WI (US); University of Hamburg, Hamburg (DE)

(72) Inventors: Robert H. Blick, Hamburg (DE); Abhishek Bhat, Madison, WI (US); Paul Gwozdz, Hamburg (DE)

(73) Assignees: Wisconsin Alumni Research Foundation, Madison, WI (US); University of Hamburg, Hamburg (DE)

( * ) Notice: Subject to any disclaimer, the term of this patent is extended or adjusted under 35 U.S.C. 154(b) by 162 days.

(21) Appl. No.: 14/444,079

(22) Filed: Jul. 28, 2014

(65) Prior Publication Data
US 2016/0025655 A1    Jan. 28, 2016

(51) Int. Cl.
| | |
|---|---|
| C12M 1/00 | (2006.01) |
| C12M 1/34 | (2006.01) |
| C12Q 1/68 | (2006.01) |
| G01R 27/08 | (2006.01) |
| C07H 21/02 | (2006.01) |
| G01N 22/00 | (2006.01) |
| G01R 23/02 | (2006.01) |
| G01N 33/487 | (2006.01) |

(52) U.S. Cl.
CPC ........ *G01N 22/00* (2013.01); *G01N 33/48721* (2013.01); *G01R 23/02* (2013.01)

(58) Field of Classification Search
CPC ........... C12M 1/00; C12M 1/34; C12Q 1/68; Y10S 977/734; C40B 30/06; G01R 27/08; G01N 33/487

USPC ....... 435/6.8, 283.1, 287.1, 287.2; 536/23.1; 324/707; 977/773

See application file for complete search history.

(56) References Cited

U.S. PATENT DOCUMENTS

| | | | | |
|---|---|---|---|---|
| 9,086,401 | B2 * | 7/2015 | Blick | G01R 31/31708 |
| 9,322,820 | B2 * | 4/2016 | Blick | G01N 33/48721 |
| 2002/0098526 | A1 * | 7/2002 | Bamdad | B82Y 30/00 435/7.9 |
| 2012/0267260 | A1 * | 10/2012 | Dharia | G01N 33/48728 205/787 |
| 2014/0253153 | A1 * | 9/2014 | Blick | G01R 31/31708 324/707 |
| 2014/0266147 | A1 | 9/2014 | Blick et al. | |

FOREIGN PATENT DOCUMENTS

WO    2008102120 A1    8/2008

OTHER PUBLICATIONS

Bhat et al.; Radio Frequency Tank Circuit for Probing Planar Lipid Bilayer Formation, A. Bhat, H. Qin, J. Rodriguez, H.C. Shin, H. Shin, D. Kreft, J. Park, E. Stava, M. Yu, and, R.H. Blick, Soft Nanoscience Letters 3, 87-92 (2013) US.

Stava et al.; Rapid fabrication and piezoelectric tuning of micro- and nanopores in single crystal quartz, Eric Stava, Minrui Yu, Hyun Cheol Shin, Hyuncheol Shin, Dustin Kreft, and Robert H. Blick, Lab Chip 13, 156-160 (2013) US.

(Continued)

*Primary Examiner* — Narayan Bhat
(74) *Attorney, Agent, or Firm* — Boyle Fredrickson, S.C.

(57) ABSTRACT

An electrically conductive nanoscale sensor includes a nanoscale pore that may be employed as a first antenna to provide precise localized measurements of the impedance-altering characteristics of a molecule such as DNA or RNA or the like passing through the pore. The use of radiofrequency measurements via a second antenna communicating with the first antenna promises high-speed analysis of long molecules (polymers).

12 Claims, 3 Drawing Sheets

(56) References Cited

OTHER PUBLICATIONS

Kim et al.; Radio Frequency Response of Single Pores and Channels, H.S. Kim, S. Ramachandran, E. Stava, D.W. van der Weide, and R.H. Blick, New Journal of Physics 13, 093033 (2011); US.
Ramachandran et al.; Direct Microwave Transmission Measurement on Single α-HL pores. S. Ramachandran, D.W. van der Weide, and R.H. Blick, Applied Physics Letters 99, 093105 (2011) US.
Hall et al.; U.S. Appl. No. 13/786,880, filed Mar. 15, 2013.
Stava et al.; Mechanical actuation of ion channels using a piezoelectric planar patch clamp system, E. Stava, M. Yu, H.C. Shin, H. Shin, J. Rodriguez, and R. H. Blick, Lab Chip 12, 80-87 (2012), DOI: 10.1039/C1LC20636B; Advance Article; US.
E.S. Sadki et al.; "Embedding a carbon nanotube across the diameter of a solid state nanopore." Journal of Vacuum Science & Technology B 29, No. 5; pp. 053001-1 thru 053001-4; (Sep./Oct. 2011): Cambridge, MA.

\* cited by examiner

RADIO-FREQUENCY NANOPORE SENSOR

STATEMENT REGARDING FEDERALLY SPONSORED RESEARCH OR DEVELOPMENT

N/A

CROSS REFERENCE TO RELATED APPLICATION

N/A

BACKGROUND OF THE INVENTION

The present invention relates to a system for the direct sequencing of polymers such as DNA and RNA and proteins by passing the polymer through a nanoscale pore and measuring an electrical signal modulated by the polymer passing through the pore.

Genetic information may be encoded in a molecule of deoxyribonucleic acid (DNA) as a sequence of nucleotides: (guanine, adenine, thymine, and cytosine). Discovering the sequence of these nucleotides in DNA and other similar molecules is a foundational technology in biological studies.

One promising method of sequencing is "nanopore sequencing" in which a single strand of DNA, forming half of the DNA helix, is passed through a nanoscale opening in a membrane between two reservoirs. This nanopore opening may, for example be a biological pore, a solid state pore, a semiconductor pore (nano-channel) or a DNA synthesized channel held in a lipid bilayer. By a drying force, e.g. an electrical potential applied across the reservoirs, an ion flow is produced between the reservoirs pulling the strand of DNA through the nanopore. As the strand passes through the nanopore, it modulates the ion current through the nanopore as a function of the size of the nucleotide, which partially obstructs the nanopore. This fluctuation in the ion current may then be analyzed to determine the nucleotide sequence. An example system of nanopore sequencing is described in PCT patent publication WO2008102120 entitled: Lipid Bilayer Sensor System, hereby incorporated by reference.

The electrical signals produced by changes in ion current through a nanopore with different nucleotides are very small in amplitude and most importantly short in time span. For this reason, it can be hard to obtain reliable measurements having sufficient resolution to distinguish between different molecules in the sequence.

U.S. patent application Ser. No. 13/786,880, assigned to the assignee of the present application and hereby incorporated by reference, describes a method of analyzing the operation of nanopore ion channels using changes in impedance of a nanopore device measured at radio frequencies.

SUMMARY OF THE INVENTION

The present invention applies the radiofrequency measurement technique of U.S. patent Ser. No. 13/786,880 to highly sensitive analysis of molecules flowing through a nanopore by using a conductive nanopore to create a nanopore antenna. Changes in the apparent impedance of the nanopore antenna coupled to a second antenna as is coupled to the molecule reveal the passage and characteristics of molecules passing through the nanopore antenna.

Specifically, the present invention provides a nanochannel sensor having a first antenna structure using an electrically conductive nanoscale pore. The conductive nanoscale pore is supported to provide a passage through the membrane between the first and second membrane side and a second antenna structure is positioned to electrically couple with the nanoscale pore. The second antenna structures are adapted to communicate with a measurement circuit producing a radiofrequency signal and measuring a change in the reflected, transmitted or radiated electrical radiofrequency signal with the passage of the molecule through the first antenna structure.

It is thus a feature of at least one embodiment of the invention to provide an improved and high-speed method of analyzing molecules such as DNA. RNA and the like. Unlike current pore-current measurement systems, the radiofrequency measurement system of the present invention promises much higher measurement speeds. It should be noted that in current systems the diffusion speed of the molecule to be screened has to be strongly reduced.

The electrically conductive nanoscale pore may have an internal diameter of less than three nanometers.

It is thus a feature of at least one embodiment of the invention to provide a nanopore antenna that can isolate individual molecular strands for measurement. It is another feature of at least one embodiment of the invention to provide an antenna structure that is significantly affected by changes due to the molecule passing through the antenna.

The electrically conductive nanoscale pore may be a biomolecule formed into a pore and coated with metallic nanoparticles. In one example, the electrically conductive nanoscale pore may be constructed of DNA with metal particles attached to it.

It is thus a feature of at least one embodiment of the invention to provide a method of fabricating conductive structures of the necessary scale.

The DNA may be modified to provide side chains presenting sulfur groups and the metal particles may be gold particles It is thus a feature of at least one embodiment of the invention to provide a method of fabricating metallized DNA structures suitable for constructing nanoscale antennas.

The nanoscale pore may include one or more conductive side antenna structures extending perpendicular to the pore axis.

It is thus a feature of at least one embodiment of the invention to significantly increase the coupling to the nanoscale antenna by increasing its extent with respect to a wavelength of an electromagnetic signal developed perpendicular to the pore axis.

The nanoscale pore can be made of semiconductor material, which functions as an antenna via regulation of the semiconductor doping.

It is thus a feature of at least one embodiment of the invention to permit the use of a variety of nanoscale pore materials.

The second antenna structure may provide a gap along a third axis across which an electromagnetic field is generated by the measurement circuit and the nanoscale pore may be oriented so that the second axis is aligned with the third axis.

It is thus a feature of at least one embodiment of the invention to significantly increase the coupling of the nanoscale antenna by adjusting its orientation with respect to a developed electromagnetic signal by the second antenna.

The nanochannel sensor may further include measurement circuitry providing a radiofrequency signal source and measuring a change in the reflected, transmitted or radiated electrical radiofrequency signal of the second antenna due to the passage of molecules through the nanoscale pore of the first antenna.

It is thus a feature of at least one embodiment of the invention to provide an integrated system for measuring the property of molecules passing through the nanopore antenna.

The measurement circuitry may monitor a change in the resonant frequency of the coupled first and second antenna system.

It is thus a feature of at least one embodiment of the invention to provide measurement that may be accomplished at high speed commensurate with radiofrequency signals.

The electrically insulating membrane may be a lipid bilayer.

It is thus a feature of at least one embodiment of the invention to provide a fluid-resistant surface that may be readily integrated with a biomolecule nanopore.

These particular features and advantages may apply to only some embodiments falling within the claims and thus do not define the scope of the invention.

DETAILED DESCRIPTION OF THE PREFERRED EMBODIMENT

Figure 1:
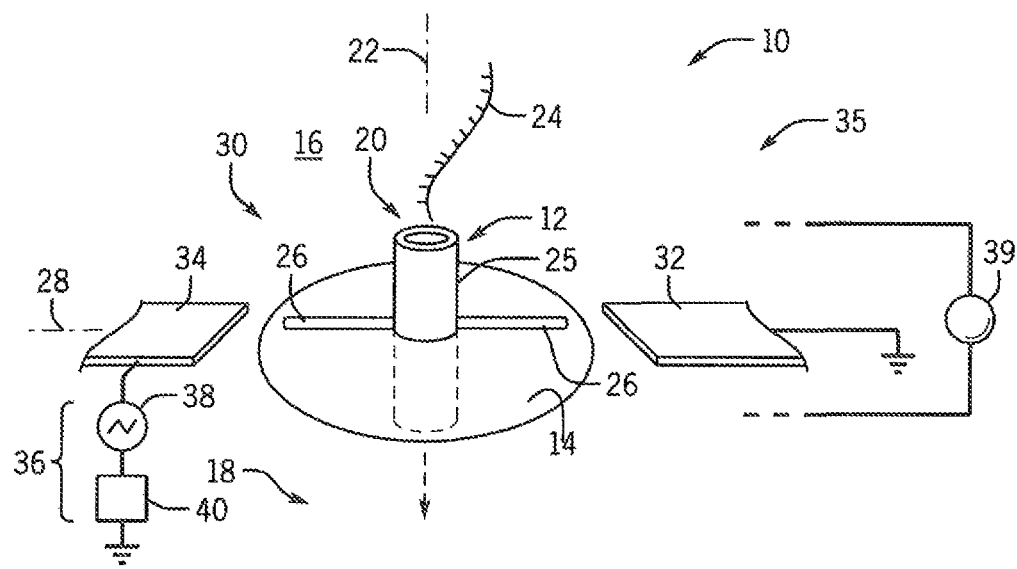
FIG. 1 is a simplified perspective view of a nanochannel sensor of the present invention providing a conductive nanopore suspended across a gap in an interrogation antenna and separating two chambers to receive a biomolecule passing between the chambers for sequencing.

Referring now to FIG. 1, a nanochannel sensor 10 may provide for an electrically conductive nanopore 12 supported on a membrane 14, the latter separating a first chamber 16 on the first side of the membrane 14 from a second chamber 18 on a second side of the membrane. The chambers may hold, for example, a fluid such as a saline solution in which biomolecules to be analyzed may be suspended.

As supported, the nanopore 12 extends generally perpendicularly through the membrane 14 to provide a through-channel 20 through the membrane 14 along a transfer axis 22 generally perpendicular to the upper face of the membrane 14 and suitable for passing a single strand of a biomolecule 24 such as DNA, RNA, peptides, proteins or the like. The membrane 14 may, for example, be a lipid bilayer of the type known in the art and similar to that forming a cellular membrane or may be a solid state nanomembrane into which the nanopore-12 can be inserted.].

In one embodiment, a generally cylindrical torus 25 of the nanopore 12 surrounding the through-channel 20 is attached to electrically conductive laterally extending arms 26, for example, extending in opposite directions on opposite sides of the cylindrical torus 25 in directions generally perpendicular to the transfer axis 22.

The arms 26 may lie closely proximate to the surface of the membrane 14 and may stabilize the nanopore 12 with respect to the membrane 14. The arms 26 may extend along a second axis 28 generally perpendicular to axis 22 and may lie within a gap 30 between secondary antenna lobes 32 and 34 of a driving antenna 35, the lobes 32 and 34 also lying along axis 28 positioned just outside the periphery of the membrane 14. In this way, each one of the arms 26 points respectively to a different lobe 32 and 34. The invention is not limited to this orientation however but also accommodates some misalignment. The arms 26 may also extend into the torus 25 but not into the through channel 20.

The antenna lobes 32 and 34 may be driven electrically by measuring circuit 36 providing a radiofrequency signal source 38 and measuring device 40 that together operate to generate a radiofrequency field across antenna lobes 32 and 34 and to measure the effective impedance of a system comprising the driving antenna 35 coupled to the nanopore 12 as influenced by the passage of biomolecules 24 through the through-channel 20. The measuring device 40 measures a change in the reflected, transmitted or radiated electrical radiofrequency signal from the nanopore 12 via the antenna lobes 32 and 34 with the passage of the molecule through the nanopore 12. In this regard, nanopore 12 forms a driven nanopore antenna structure coupled to the driving antenna 35 of lobes 32 and 34. The arms 26 improve the coupling between the nanopore 12 and the driving antenna 35 of lobes 32 and 34.

Biomolecules 24 may be encouraged through the through-channel 20 from chamber 16 to chamber 18 by a number of different means including, for example, a slight electrical bias between chambers 16 and 18 provided by DC biasing source 39 such as may act upon ions and charged molecules under test (DNA) within fluids of the chambers 16 and 18.

Figure 2:
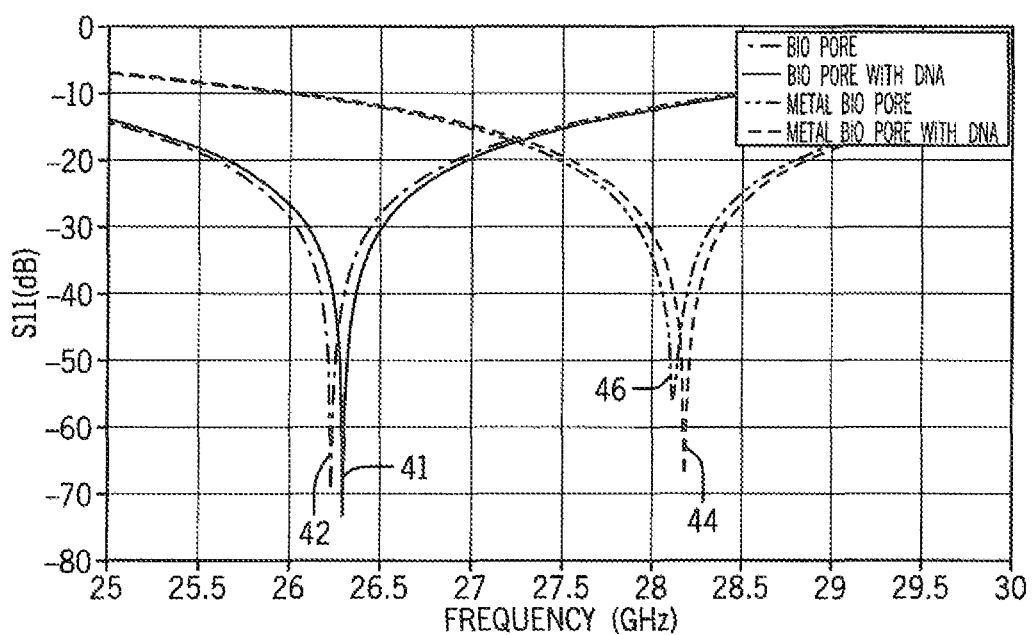
FIG. 2 is a plot of reflectance versus frequency for the system of FIG. 1 showing variations in the measurements associated with a metallized and non-metallized nanopores with and without the passage of DNA therethrough.

Referring to FIG. 2, theoretical evidence indicates that the use of an electrically conductive nanopore 12 substantially increases the quality (Q) factor of a resonant circuit created by the system of the driving antenna 35 and the nanopore 12. A plot of an attenuation of the radiofrequency signal from the radiofrequency signal source 38 versus frequency of that radiofrequency source 38 shows its natural resonance in the form of a negative-going "trough" 41 that is sharper and larger with the metallized nanopore 12 as compared to a resonant trough 42 for a nanopore that is not electrically conductive. Similar troughs 44 for the conductive nanopore 46 and for a nonconductive nanopore both with DNA passing through the nanopores are also shown indicating the effect of the presence of a biomolecule within the nanopore through-channel 20. Measurement of the nanopore 12 may analyze the biomolecule through any one or more of frequency change of these peaks and/or the amplitude change in these peaks and/or phase change of the signal or the like known in the art.

Figure 3:
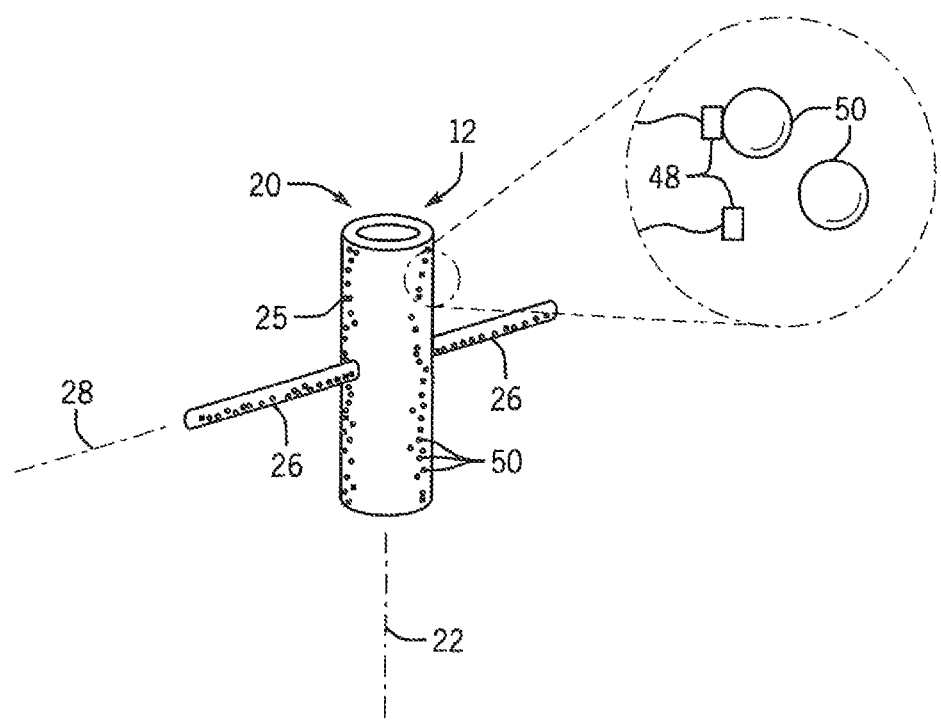
FIG. 3 a simplified diagram of the metallization of the nanopore formed from DNA.

Referring now to FIG. 3, in one embodiment, the cylindrical torus 25 of the nanopore 12 may be fabricated of DNA using DNA-prototyping, for example, as described in Synthetic Lipid Membrane Channels Formed by Designed DNA Nanostructures, Martin Langecker et al., Science 338, 932 (2012); DOI: 10.1126/science.1225624 hereby incorporated by reference. An average diameter of the through-channel 20 of the nanopore 12 will be such as to limit the passage through the through-channel 20 of a single biomolecule of interest and will typically be less then three nanometers or preferably less than two nanometers in diameter. The height of the cylindrical torus 25, in one embodiment, as measured along the transfer axis 22 may be at least five nanometers and typically 10 to 20 nanometers and an outer diameter of the cylindrical torus 25 may be greater than five nanometers and typically 5 to 20 nanometers. The arms 26 are constructed of DNA strands attached to the cylindrical body as discussed above. The arms 26 will generally extend by an amount no less than five nanometers from the transfer axis 22.

Electrical conductivity of the structure of the cylindrical body and arms 26 is provided by replacing side chains of the DNA molecule of the cylindrical body and arms 26 with sulfur groups 48 which will link to gold nanoparticles 50 applied to the nanopore 12.

Alternatively the cylindrical torus 25 may be a wild-type or genetically engineered nanopores such as α-hemolysin or a semiconductor nanotubes such as carbon nanotubes or colloidally grown nanotubes.

Figure 4:
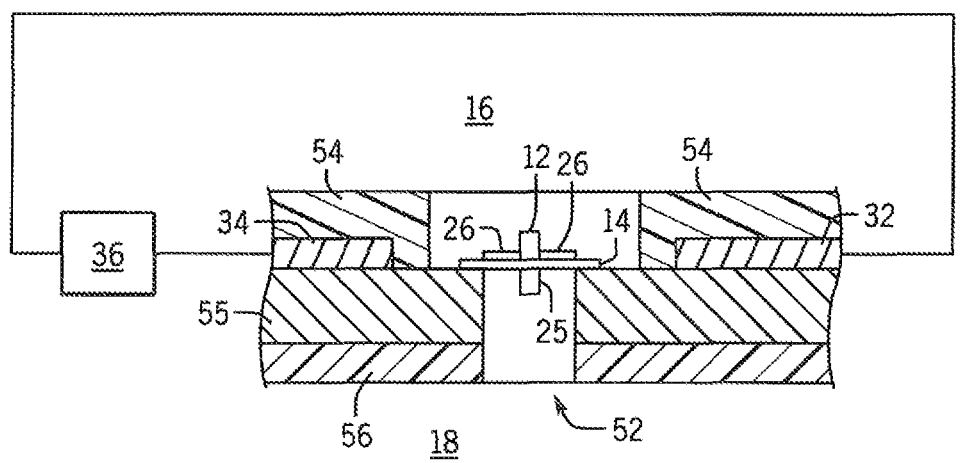
FIG. 4 is an elevational cross-section of a nanopore and interrogation antenna system used for nanopore measurement.

Referring now to FIG. 4, the membrane 14 may be supported at its periphery on an opening 52 in an insulating planar support 55 such as a glass or quartz plate with the antenna lobes 32 and 34 being conductive traces deposited on the upper surface of the planar support 55 closely adjacent to the edges of the opening 52. The membrane 14 may be attached to the opening 52 by painting or by applying vesicles of lipid bilayers The conductive material of the lobes 32 and 34 may be a variety of different metals including aluminum, copper, silver, gold and the like or conductive metal compounds such as silver chloride.

An electrically insulating layer 54 may cover the lobes 34 and 32 against electrical contact with the liquid in chamber 16. The electrically insulating layer 54 may, for example, be a thin coating of Parylene-C commercially available from a number of suppliers A similar insulating layer 56 may be applied on the lower surface of the planar support 55.

Figure 5:
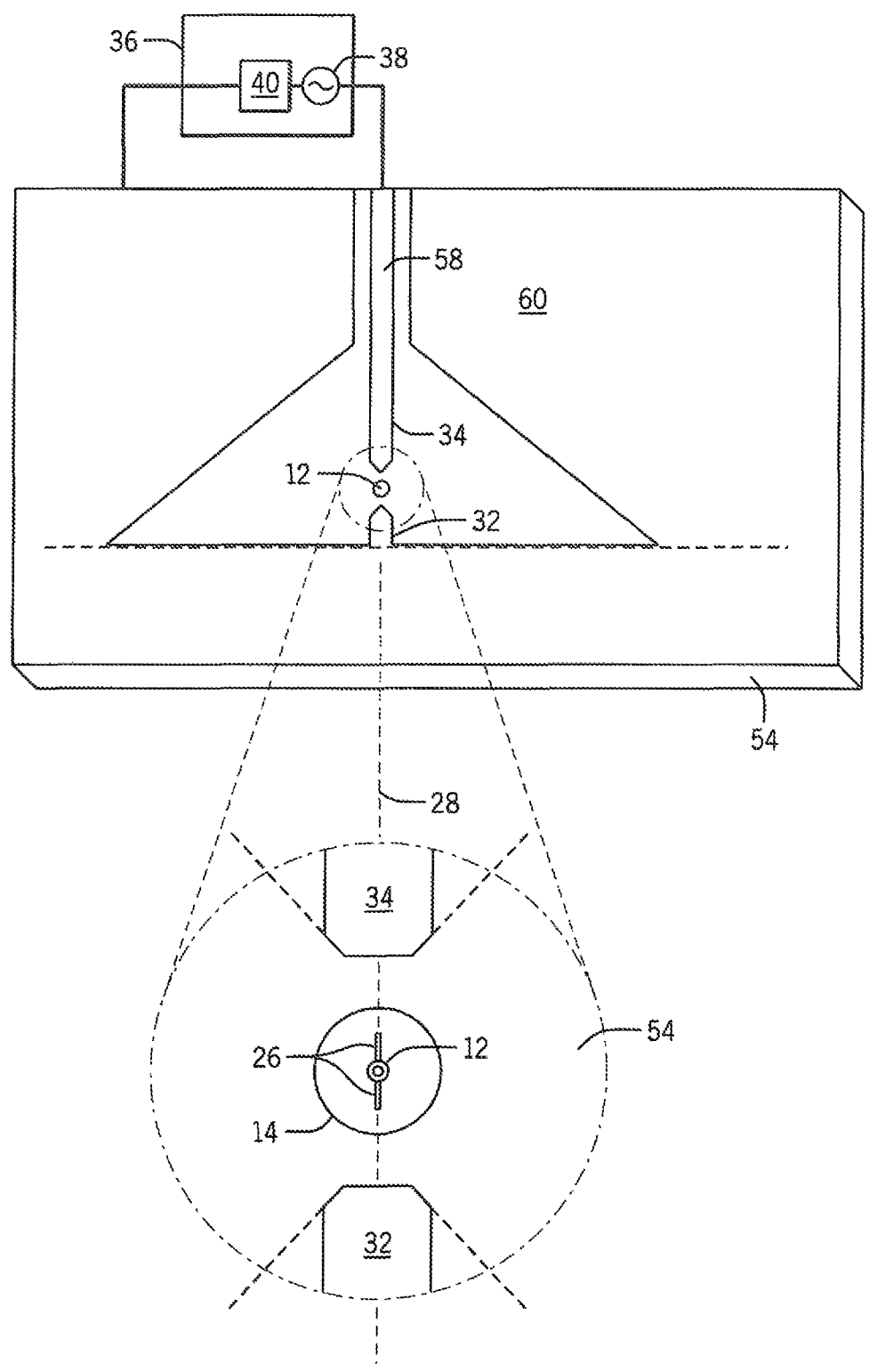
FIG. 5 is a perspective top view of the interrogation antenna system with a fragmentary detail showing the nanopore.

Referring now to FIG. 5, the lobes 34 and 32 may provide a bowtie antenna in which electrode lobe 34 connects to measuring circuit 36 by a conductor 58 passing along an upper surface of the insulating planar support 55 along axis 28 as flanked on either side by a ground plane conductor 60. As conductor 58 approaches the nanopore 12, it forms lobe 34 and the ground plane conductor 60 diverges from axis 28 (for example, by opposite angles of 45 degrees) to a point past the lobe 32. The ground plane conductor 60 then converges to rejoin on the left and right side of axis 28 to attach to the end of lobes 32 removed from the nanopore 12 to provide a "bowtie" type antenna.

The concept of measuring the electrical properties of the nanopore 12 should be understood to include both direct and indirect measurements and to consider radiofrequency energy that is reflected, transmitted or radiated by the nanopore 12.

It will be appreciated that additional side arms 26 may be added to the cylindrical torus 25 so as to promote increased coupling with the electromagnetic field developed between the lobes 32 and 34 of the driving antenna 35.

The following documents describing previous work by the inventors and are hereby incorporated by reference:

Radio Frequency Tank Circuit for Probing Planar Lipid Bilayer Formation', A. Bhat, H. Qin, J. Rodriguez, H. C. Shin, H. Shin, D. Kreft, J. Park, E. Stava, M. Yu, and, R. H. Blick, Soft Nanoscience Letters 3, 87-92 (2013); DOI: 10.4236/snl.2013.34016

'Rapid fabrication and piezoelectric tuning of micro- and nanopores in single crystal quartz', Eric Stava, Minrui Yu, Hyun Cheol Shin, Hyuncheol Shin, Dustin Kreft, and Robert H. Blick, Lab Chip 13, 156-160 (2013): DOI: 10.1039/ C2LC40925A. http://pubs.rsc.org/ doi: 10.1039/ C2LC40925A 'Mechanical actuation of ion channels using a piezoelectric planar patch clamp system', E. Stava, M. Yu, H. C. Shin, H. Shin, J. Rodriguez, and R. H. Blick, Lab Chip 12, 80-87 (2012), DOI: 10.1039/C1LC20636B; Advance Article— inside cover title (http://pubs.rsc.org/en/content/articleland-ing/2012/lc/c1lc90128a); DOI: 10.1039/C1LC90128A.

'Radio Frequency Response of Single Pores and Channels', H. S. Kim, S. Ramachandran, E. Stava, D. W. van der Weide, and R. H. Blick, New Journal of Physics 13, 093033 (2011); http://iopscience.iop.org/1367-2630/13/9/093033/; DOI: 10.1088/1367-2630/13/9/093033.

'Direct Microwave Transmission Measurement on Single α-HL pores', S. Ramachandran, D. W. van der Weide, and R. H. Blick, Applied Physics Letters 99, 093105 (2011); DOI.org/10.1063/1.3626586.

The term "electrically conductive" applied to the nanopore means an electrical conductivity suitable for generating measurable antenna currents and typically exceeding that of unmodified DNA. It is expected that the production of an electrically conductive nanopores suitable for this purpose will require the introduction of foreign conductive materials such as metals to a DNA structure or construction of the nanopore of a conventionally conductive material.

Certain terminology is used herein for purposes of reference only, and thus is not intended to be limiting. For example, terms such as "upper," "lower," "above," and "below" refer to directions in the drawings to which reference is made. Terms such as "front," "back," "rear," "bottom," "side," "left" and "right" describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first," "second" and other such numerical terms referring to structures do not imply a sequence or order unless clearly indicated by the context.

When introducing elements or features of the present disclosure and the exemplary embodiments, the articles "a," "an," "the" and "said" are intended to mean that there are one or more of such elements or features. The terms "comprising," "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

All of the publications described herein including patents and non-patent publications are hereby incorporated herein by reference in their entireties.

We claim:

1. A nanochannel sensor comprising:
    a first antenna structure providing an electrically conductive material defining a nanoscale through-channel;
    a membrane having a first side and a second side and supporting the first antenna structure so that the through-channel provides a passage through the membrane between the first side and second side; and
    a second antenna structure proximate to the first antenna structure to electrically couple radiofrequency signals between the first antenna structure and the conductive material of the second antenna structure;

wherein the second antenna structure is configured to communicate with a measurement circuit producing a radiofrequency signal and measuring a change in the radiofrequency signal with the passage of a molecule through the nanoscale through-channel of the first antenna structure caused by a change in impedance of the electrically conductive material of the first antenna structure as coupled to the second antenna structure and the molecule;

wherein the nanoscale through-channel further comprises a nanoscale pore formed by a biomolecule coated with metallic nanoparticles; and wherein the nanoscale pore has an internal diameter of less than three nanometers.

2. The nanochannel sensor of claim 1 wherein the biomolecule is a DNA with metal particles attached to it.

3. The nanochannel sensor of claim 2 wherein the metal particles are gold particles.

4. The nanochannel sensor of claim 1 wherein the nanoscale through-channel of the first antenna structure extends generally along a first axis and further including at least one conductive side antenna arm extending along a second axis perpendicular to the first axis away from an axis of the nanoscale through-channel toward the second antenna structure.

5. The nanochannel sensor of claim 4 wherein the second antenna structure provides a gap along a third axis across which an electromagnetic field is generated by the measurement circuit and wherein the nanoscale through-channel is oriented so that the second axis is substantially aligned with the third axis.

6. The nanochannel sensor of claim 4 wherein the first antenna structure includes at least two side conductive arms extending along the second axis from opposite sides of the first antenna structure.

7. The nanochannel sensor of claim 1 wherein the measurement circuit further comprises a radiofrequency signal source and measuring a change in the reflected, transmitted or radiated electrical radiofrequency signal of the second antenna structure with the passage of the molecule through the nanoscale through-channel of the nanoscale pore.

8. The nanochannel sensor of claim 7 wherein the measurement circuitry monitors at least one of a change in natural resonant frequency, a change in signal amplitude, and a change of phase of the radiofrequency signal by the first and second antenna structures.

9. The nanochannel sensor of claim 1 wherein the membrane is a lipid bilayer.

10. The nanochannel sensor of claim 1 wherein the nanoscale through-channel includes a substantially cylindrical torus having a height of at least five nanometers.

11. The nanochannel sensor of claim 10 wherein the first antenna structure has an outer diameter of at least five nanometers.

12. A method of sensing molecules using a nanochannel sensor having:
    a first antenna structure providing an electrically conductive material defining a nanoscale through-channel;
    a membrane having a first side and a second side and supporting the first antenna structure so that the through-channel provides a passage through the membrane between the first side and second side; and
    a second antenna structure proximate to the first antenna structure to electrically couple radiofrequency signals between the first antenna structure and the conductive material of the second antenna structure;
    wherein the second antenna structure is configured to communicate with a measurement circuit producing a radiofrequency signal and measuring a change in the radiofrequency signal with the passage of a molecule through the nanoscale through-channel of the first antenna structure caused by a change in impedance of the electrically conductive material of the first antenna structure as coupled to the second antenna structure and the molecule;
    wherein the nanoscale through-channel further comprises a nanoscale pore formed by a biomolecule coated with metallic nanoparticles; and
    wherein the nanoscale pore has an internal diameter of less than three nanometers, the method comprising the steps of:
    (a) applying the radiofrequency signal to the second antenna structure;
    (b) sampling an impedance of the second antenna structure at multiple points in time; and
    (c) identifying molecules passing through the nanopore sensor based on changes in the reflected, transmitted or radiated electrical radiofrequency signal of the second antenna structure with the passage of the molecule through the first antenna structure.

* * * * *